United States Patent [19]

Uemura et al.

[11] 4,356,827

[45] Nov. 2, 1982

[54] METHOD OF ARRHYTHMIA DETECTION WITH DETECTING MECHANISM

[75] Inventors: Masahiro Uemura, Kasugai; Chikao Harada, Aichi; Kenichi Sakurado, Mizunami; Tsunehito Kakamu, Gifu, all of Japan

[73] Assignee: Nippon Collin Co., Ltd., Komaki, Japan

[21] Appl. No.: 187,723

[22] Filed: Sep. 16, 1980

Related U.S. Application Data

[62] Division of Ser. No. 963,966, Nov. 27, 1978, Pat. No. 4,262,674.

[51] Int. Cl.³ .............................................. A61B 5/02
[52] U.S. Cl. ..................................... 128/680; 128/681
[58] Field of Search ................................ 128/680-683, 128/702-703, 705

[56] References Cited

U.S. PATENT DOCUMENTS

| | | | |
|---|---|---|---|
| 3,791,378 | 2/1974 | Hochberg et al. | 128/682 |
| 3,996,928 | 12/1976 | Marx | 128/683 X |
| 4,073,011 | 2/1978 | Cherry et al. | 128/702 X |
| 4,105,020 | 8/1978 | Matsuoka et al. | 128/682 |
| 4,216,779 | 8/1980 | Squires et al. | 128/682 |

FOREIGN PATENT DOCUMENTS 2618323 11/1977 Fed. Rep. of Germany ...... 128/680

*Primary Examiner*—Kyle L. Howell
*Assistant Examiner*—Francis J. Jaworski
*Attorney, Agent, or Firm*—Browdy and Neimark

[57] ABSTRACT

A method of using a sphygmomanometer having a built-in arrhythmia detecting mechanism, wherein the blood pressure measuring portion contains a pulsation detector, which receives pulse sounds including Korotkoff sounds for electrically converting the pulse sounds into wave form signals of the vascular pulse wave and output the same, and a mechanism indicating the blood pressure value by means of detecting the Korotkoff sounds recognized and separated from the wave form signals of the vascular pulse wave output in the above-mentioned way; the incorporated arrhythmia detecting mechanism receives the wave form signals of the vascular pulse wave for comparing the cycle of the wave form signals with a predetermined criterion in order to electrically detect irregularities, if any, in the signals for detecting the existence of arrhythmias. This sphygmomanometer is capable of measuring the blood pressure simultaneously with the detecting of arrhythmia.

11 Claims, 5 Drawing Figures

METHOD OF ARRHYTHMIA DETECTION WITH DETECTING MECHANISM

This is a division of application Ser. No. 963,966 filed Nov. 27, 1978 and issued as U.S. Pat. No. 4,262,674.

BACKGROUND OF THE INVENTION

The present invention relates to a sphygmomanometer, which is concurrently capable of detecting arrhythmia, or pulse irregularities. More particularly, it relates to an instrument for detecting and indicating the Korotkoff sounds for the purpose of measuring blood pressure, which concurrently functions as a detector and as an indicator of arrhythmia.

Often during general medical check-up or diagnosis blood pressure is measured with a sphygmomanometer. It is of course an indispensable step during medical examinations of elderly patients.

If blood pressure and arrhythmia which is closely related with the blood pressure trend can be measured simultaneously with a single instrument or apparatus, it would be very convenient and would contribute much to the improvement of the medical examination. No conventional sphygmomanometer is known capable of easily detecting the arrhythmia. None of the known arrhythmia detecting instruments is capable of measuring the blood pressure simultaneously.

Blood pressure has been traditionally determined by measuring the maximum and minimum value thereof employing an indirect method of listening to the appearance and disappearance of the so-called Korotkoff sounds. A kind of elongated air bag called a cuff is wound around an arm of a human body and air is sent thereinto to build up a pressure until the blood flowing in the artery is stopped, and then the air pressure is gradually decreased. At some point Korotkoff sounds (i.e. frictional sounds between the artery wall and the flowing blood) begin to be heard when the systolic blood pressure is measured. Afterwards, the air pressure is further decreased until the Korotkoff sounds disappear which is the point when the diastolic blood pressure can be measured.

Pulses including Korotkoff sounds of such type can be usually collected by a pulse detector or sensor with a microphone (called a pick-up), to be electrically transformed into a wave signal of the vascular pulse wave. As a pulse detector, U.S. Ser. No. 722,122 "Vascular Sound Detector", now U.S. Pat. No. 4,141,350 to Shinoda et al. which has been assigned to the same assignee as that of the present application, or other disclosures can be seen. The output from this kind of detector in a form of a wave signal is electrically treated for furnishing Korotkoff sounds, in a separate or recognizable form, which enables the measurement of the blood pressure desired to be performed.

Sphygmomanometers of such a structure are disclosed and some of them are already on the market. By way of example, TOKU-KAI-SHO-No. 52 (1977)-84886 (Japan), "Sphygmomanometer", which has been assigned to the same assignee to that of the present application, is a device wherein pulse-sound-signal and Korotkoff-sound-signal (frictional sound between the artery wall and the flowing blood) can be selected or separated according to the form of the vascular pulse wave, and the two types of wave signal are led through an electronic circuit to two differently colored light emitting diodes. This instrument is capable of indicating, for example, the pulse sound signal in red and the Korotkoff sound signal in blue, i.e., indicating by color the appearance and the disappearance of Korotkoff sounds, the diastolic and systolic blood pressure being indicated on a visually readable numerical display.

Another example, TOKU-KAI-SHO-No. 52 (1977)-84885 (Japan), "Indicator for short of pressure-rising in an Automatic Sphygmomanometer" which has been assigned to the same assignee to that of the present application, is of a mechanism, wherein the cuff pressure can be automatically and progressively raised until it reaches a suitable pressure for initiating measurement of the blood pressure.

On the other hand, various instruments or devices are already disclosed as to the recognition of the arrhythmia, such as frequent pulses, and infrequent pulses, and irregular pulses. Against the normal pulsation rhythm, a repeated dual-type pulsation of 60 to 80 times per minute, pulsation more than 100 per minute is defined as frequent, pulsation less than 50 per minute infrequent, and other irregularities, for instance, triple or quadruple rhythm are also defined as arrhythmia in a narrow sense.

Instruments for detecting arrhythmia are generally so deigned as to perform electrical detection of pulsation irregularities by means of electrically comparing the period of vascular pulsation of a subject with a predetermined criterion or standard, i.e., by electrically detecting the degree of deviatin from the criterion.

Taking an interval of two neighboring pulsations, or an average interval of several consecutive pulsations, as a standard value for converting it into a clock pulse number of a certain frequency, and two values calculated by adding and substracting one to and from every N clock pulses shall be memorized by a memory storage as the upper and lower limits for the jugement. The arrhythmia is judged by comparing the clock pulse number of the next pulse interval with this criterion. Another way of discovering an arrhythmia is enacted by letting a memory storage memorize in advance a standard period or cycle of the pulse signal (for example in a form of clock pulses) corresponding to a vascular pulse, after increasing or decreasing by a certain percentage to and from the standard pulse number for setting the upper and lower limits for the comparison, i.e., a window comparator. Comparing the pulse signals with the standard frame set on the window comparator, arrhythmia can be recognized.

As above-mentioned, sphygmomanometers as such and detectors of arrhythmia respectively have been developed so far. In both fields various excellent instruments have been disclosed and provided on the market. As an individual instrument most of them are satisfactory. Combined instruments capable of functioning in two ways, i.e., adapted to accomplish both objects, have never been developed heretofore, despite the fact that the individual mono-purpose devices are excellent and despite the fact that both instruments are used during one examination of one patient quite often.

SUMMARY OF THE INVENTION

While studying the actual circumstances in the medical field, the inventors thought of combining the two instruments to create a sphygmomanometer with a detector of arrhythmia, and found it would contribute to actual medical examinations far more than expected. The invention was made from such a background.

It is therefore a basic object of this invention to provide a method of sphygmomanometer use concurrently capable of detecting arrhythmia.

It is an important object of this invention to provide a method of the character described utilizing sphygmomanometer combining a pulse sound pick-up, a Korotkoff sound recognizing circuit, and a blood pressure indicator, concurrently provided with an arrhythmia detector and its indicator, whereby the instrument is capable of measuring blood pressure as well as diagnosing arrhythmia simultaneously.

It is another object of this invention to provide method of the character described utilizing a sphygmomanometer equipped with an arrhythmia detector, which is far less expensive, far easier in handling, far more convenient in clinical use and in carrying, while maintaining sufficient precision in the actual measurement in comparison to the conventional ones.

Other objects and features of this invention will be apparent from a study of the description below with reference to the appended drawings.

The objects of this invention have been achieved by completing a blood pressure measuring instrument, including a pulsation detector, which receives pulse sounds including Korotkoff sounds, for electrically converting the same into wave signals of the vascular pulse wave in order to output them; and a mechanism for detecting the Korotkoff sounds separate from the wave signal of the vascular pulse wave output from the said pulsation detector in order to indicate the blood pressure value. The instrument is concurrently capable of diagnosing arrhythmia by incorporating an arrhythmia detecting mechanism which receives the wave signals of the vascular pulse wave output from the pulsation detector for detecting the existence of arrhythmia by comparing the cycle of the wave signals with a predetermined criterion value. In short, this invention has made it possible to conduct blood pressure measurements and the arrhythmia detection concurrently in an easy and simple way.

The objects are achieved in particular by providing a method of the character described using a sphygmomanometer comprising (1) a blood pressure measuring apparatus including a pulsation detector means which collects pulse sounds including Korotkoff sounds for electrically converting said pulse sounds into wave signals of the vascular pulse wave and outputting the same, and means for detecting the Korotkoff sounds and indicating the blood pressure value; and (2) an arrhythmia detecting means coupled to the output of said pulsation detects means, which receives said wave signals of the vascular pulse wave output from said pulsation detector means and compares the cycle of said wave signals with a predetermined criterion for electrically detecting the irregularities, if any, in said cycle. The arrhythmia detecting means comprises: a circuit for converting a pulse interval, which spans the time from a given base point of a pulse to a corresponding given base point of the next pulse, the base points being in the same phase of successive cycles, into a representative signal corresponding to said pulse interval; window comparator means for comparing the representative signal with a predetermined criterion in order to check whether the representative signal is within the limit of allowance; and an indicating means for indicating arrhythmia by means of the output of said window comparator.

The sphygmomanometer is a widely used instrument, employed daily not only in the consultation room, but also in the case of home-visiting (house-calling) as a portable instrument. The fact that this invention made it possible to measure blood pressure and to detect arrhythmia simultaneously produces benefits that had not been expected.

As the secondary effects of this instrument, in addition to the essential effect of capability of measuring the blood pressure and the arrhythmia simply and accurately simultaneously, the following can be enumerated:

(1) The time required for fastening and unfastening the instrument to and from a patient (a subject) can be remarkably shortened, as it has to be applied only once contrary to the conventional way of requiring two application motions.

(2) The time required for measuring is also remarkably shortened, because conventionally the measuring time is of course the sum of the two procedures, but in the invention instrument the shorter time of the two procedures is naturally included in the larger one, totally saving the time required for the shorter procedure.

(3) Reduction of the total time for the measurements are both a saving of the precious time of the physician, and a relief of the often unpleasant as well as anxious time for the patient.

(4) As the sound pick-up, or a sound collecting portion is comparatively costly, the invention's double-purpose use thereof, contributes greatly to reductions in manufacturing cost; and (5) From a series of experimental uses of this instrument, many co-existent cases of the irregularities in blood pressure and arrhythmia in a same patient have been observed. If, in the future, any close co-relationship between the two irregular symptoms is theoretically proved to provide new medical problems, this double-purpose or double-functional instrument would be an extremely valuable tool in medical diagnosis.

BRIEF DESCRIPTION OF THE DRAWINGS

FIG. 4 is another block diagram showing another example of a arrhythmia detecting mechanism which is to be attached to the sphygmomanometer of this invention.

DETAILED DESCRIPTION OF THE PREFERRED EMBODIMENTS

Figure 1:
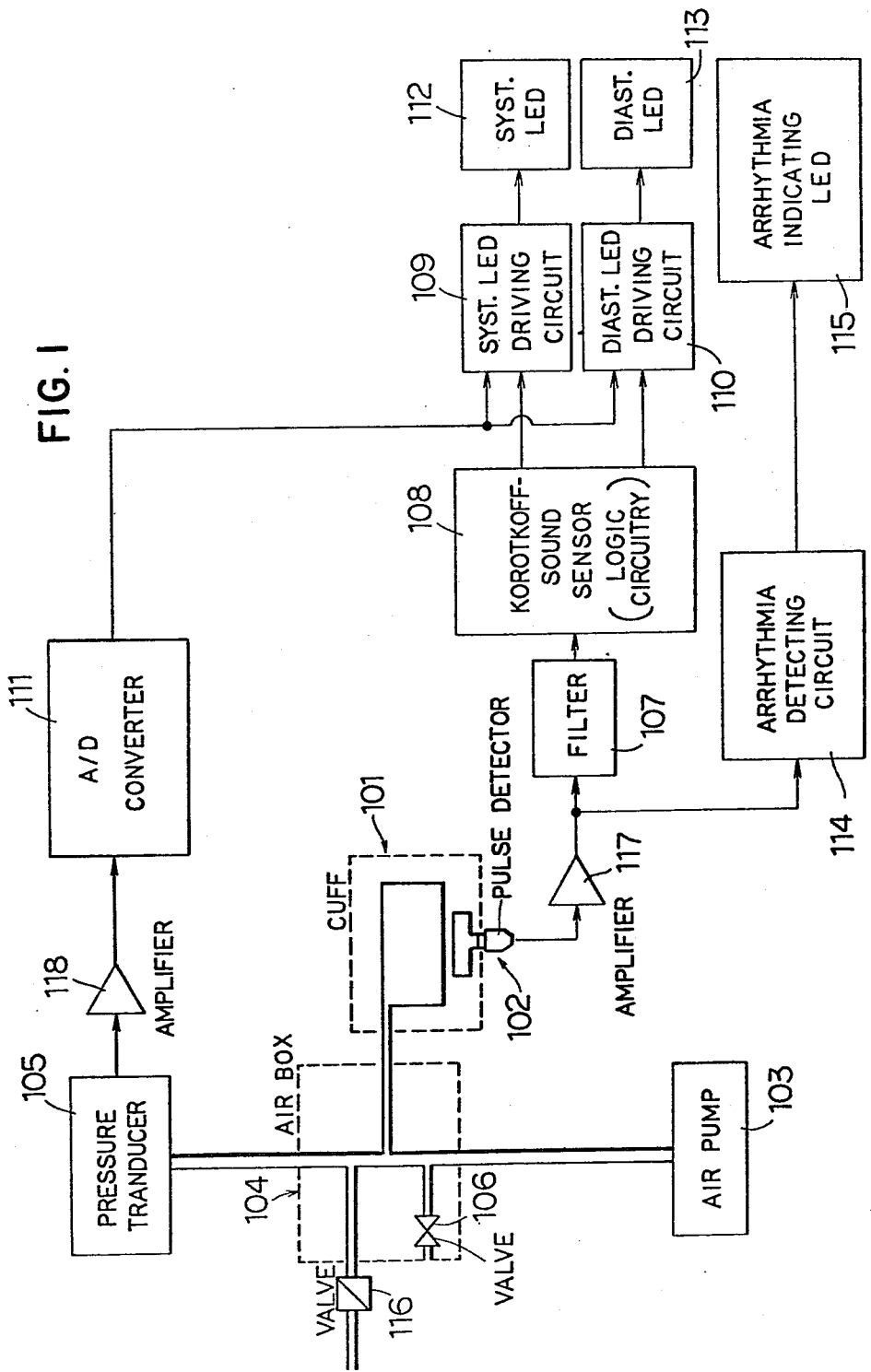
FIG. 1 is a block diagram conceptionally showing a first embodiment of a sphygmomanometer with an arrhythmia detector.

In FIG. 1, 101 is a cuff which is wound on a part of a human body, for example, on an arm for pressing the corresponding place strong enough to partially restrain the flow of the arterial blood there. In the cuff 101 a pulse detector 102 is disposed which is of identical type to that disclosed in U.S. Ser. No. 722,122 now U.S. Pat. No. 4,141,350 for picking up the pulse sound, which detector contains a microphone therein. The cuff 101 is supplied with air, by an air pump 103 driven by a motor, into its air box 104 to build up pressure therein. The degree of pressure in the cuff 101 is electrically converted by a pressure transducer 105, and the air can be released, when becomes unnecessary, by an air bleed valve 106 and a quick release valve 116 for discharging. The air bleed valve 106 is in this instance so designed as to discharge air while decreasing the inner pressure of the cuff 101 at the constant rate of approximately 3 mmHg/sec. The wave signal of the vascular pulse wave output from the pulse detector 102 is input, through a filter means 107 including a low-pass filter for pulse sound, a band-pass filter for systolic pressure, and a band-pass filter for diastolic pressure, to a logic circuitry 108 for recognizing the Korotkoff sounds. Wanted signals are sent from the logic circuitry 108 of such a structure to a driving circuit 109 for a systolic blood pressure indicating tube (LED) and a driving circuit 110 for a diastolic blood pressure indicating tube (LED). To these driving circuits 109, 110 are input electrical signals from the pressure transducer 105, via digital/analogue converter 111, thereby indicating respectively systolic and diastolic blood pressure value required on an indicator 112 and 113 in a form permitting to digitally read out with light emitting diodes (LED). Furthermore, elements 117 and 118 are amplifiers.

The wave signals of the vascular pulse wave output from the pulsation detector 102 are simultaneously input into an arrhythmia detecting circuit 114, wherein the period or cycle of the wave signals are compared with the predetermined criterion value for electrically detecting the irregularity or abnormality, if any, whereby existence of arrhythmia or the frequency thereof may be indicated by means of LED, etc. This invention is a sphygmomanometer, a device for detecting and indicating Korotkoff sounds for the purpose of blood pressure measuring, having a built-in arrhythmia detecting and indicating device therein, which consequently enables simultaneous diagonsis of arrhythmia and blood pressure measuring.

As Korotkoff sounds recognizing or separating mechanism (logic circuit 108, etc.) for blood pressure measurement, and as arrhythmia detecting mechanism (judging circuit 114), any of the well-known mechanisms or circuits may be selected and used in this invention. Although systolic blood pressure and diastolic blood pressure can be digitally indicated utilizing LEDs in this invention, it may be replaced by an indicating means employing an analogue method. Furthermore, it is also possible to carry out the input of wave signals into the arrhythmia detecting circuit 114 by way of the logic circuitry 108. It is needless to say that the instrument of this invention may be, in addition to the above-mentioned systolic and diastolic blood pressure indicating mechanism, attached some other indicating means and/or operating (computing) circuit therefor for other factors such as number of pulsations.

In this invention, i.e., a sphygmomanometer with a arrhythmia detector, it is desirable to measure blood pressure and detect arrhythmia simultaneously by means of the under-mentioned way and accessory devices. When judging an existence of arrhythmia, a comparison method is adopted, wherein a ratio of a pulse interval $T_1$ which indicates a time from a certain pulse appearance (or disappearance) point to a next similar pulse appearance (or disappearance) point versus another pulse interval $T_2$ which indicates a time taken on the similar next pulse space, is compared with a predetermined allowance value, for determining the arrhythmia by checking, that is the comparison, the ratio value not being within the allowable range of value. A first pulse is electrically formed from a pulse signal to be detected, and as an object of comparison between the pulse intervals the ratio of the two consecutive pulse intervals $(T_1 - t_1)$ and $(T_2 - t_1)$ is determined, wherein $t_1$ being the width of the first pulse. Within the duration time of a second pulse $t_2$, which is smaller in width than the first pulse $t_1$ and is triggered at the rising of the next of the first pulse but one, the aforementioned comparison is finished, and the memory of the comparison between the pulse intervals is cleared within the time from the falling of the second pulse to the falling of the firt pulse $(t_1 - t_2)$. (refer to FIGS. 3 and 5)

For carrying out such a method, it is necessary to employ a device comprising a circuit for converting a pulse interval, corresponding to a time from a certain pulse appearance (or disappearance) point to a next similar pulse appearance (or disappearance) point, to another corresponding physical amount, a window comparator for making a comparison whether the converted physical amount be within a predetermined allowance range, and means indicating the arrhythmia by means of the output of the window comparator. For such an instrument installation of the under-mentioned additional circuits is preferable:

a first pulse forming circuit for shaping the pulse signal to be detected into a rectangular wave having the width of $t_1$;

a memory circuit for memorizing the physical amount converted by the converting circuit;

a timing circuit for making at least the converting circuit and the memory circuit orderly operate without fail (to control each operation of each component element);

an operation (computing) circuit for calculating the physical amount, as the object of comparison, corresponding to a value which is respectively got by the deduction of the pulse width $t_1$ from the first pulse interval $T_1$ and the second pulse interval $T_2$;

a second pulse forming circuit for shaping the pulse signal into a rectangular wave having the pulse width $t_2$, shorter than the pulse width $t_1$, within the time of which $t_2$ the comparison of the pulse intervals can be completed, and the memory circuit can be cleared within the rest of the time $(t_1 - t_2)$; and a flip-flop circuit which takes the output from the first pulse forming circuit as its input, and outputs to the second pulse forming circuit and the timing circuit. With reference to FIGS. 2–5, more detailed description of the above-mentioned method and instrument (mechanism) will be concretely made.

Figure 2:
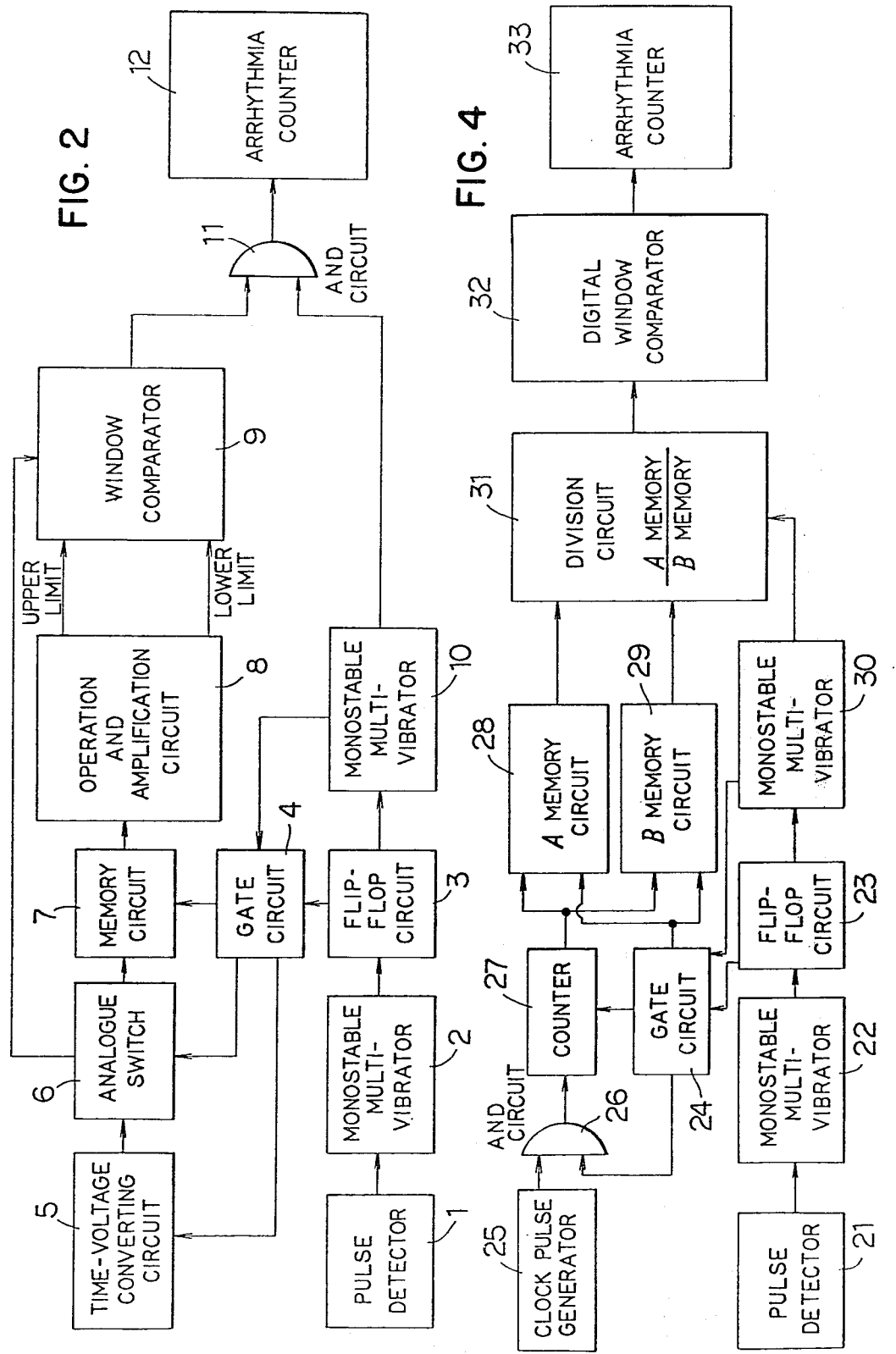
FIG. 2 is a block diagram showing an example of the mechanism of arrhythmia detector to be attached to a sphygmomanometer in accordance with this invention.
Figure 3:
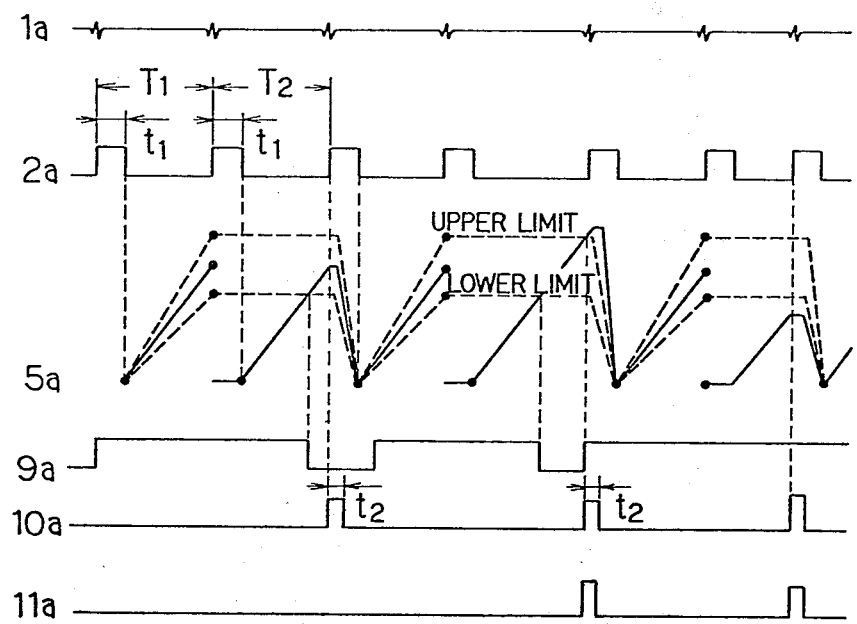
FIG. 3 is a diagram of wave forms showing phase relationship of each circuit in the arrhythmia detecting mechanism of FIG. 2.

FIG. 2 is a block diagram for explaining the operation of an embodiment of the already mentioned arrhythmia detecting mechanism; FIG. 3 is a wave diagram for showing the relation with the lapse of time.

Description will proceed based on FIG. 2, with reference to FIG. 3.

Pulse signals are electrically detected frist by a pulse detector 1 having a pick-up or other means; the output of the pulse detector 1 is to be shaped into a rectangular pulse wave of a suitable width by a first monostable multi-vibrator 2, which is a pulse shaping circuit. The pulse width $t_1$ is preferable to be limited not more than 7 milliseconds (ms) for a later stated reason.

Triggered by the falling of the rectangular wave of the pulse width $t_1$, the output of a flip-flop circuit 3 makes, by way of a gate circuit 4, a time-voltage-converting circuit 5 operate, whereby an approximate pulse interval $(T_1-t_1)$, i.e., the rest of the time a certain pulse interval $T_1$ minus pulse width $t_1$, which is to be an object of comparison, can be converted to a voltage.

The output voltage of this time voltage converting circuit 5 is, via an analogue switch 6 and being triggered by the rising of the rectangular wave, memorized by a memory circuit 7. An operation-and-amplification circuit 8 is actuated to compute, for calculating the increase and the decrease by 25% of that voltage to respectively have the upper and lower limits, which results will be memorized by a window comparator 9 as the upper and lower limits for the comparison respectively.

Consecutively, an approximate pulse interval $T_2$, which comes on after the pulse interval $T_1$, minus the pulse width $t_1$ $(T_2-t_1)$ is in the similar way converted to a voltage for being input, via an analogue switch 6, directly to the window comparator 9. After being compared with the operated (computed) upper- and lower limits value, the voltage value, when be judged to be out of the criterion range, will be so output from the window comparator 9. The gate circuit 4 functions in the meantime as a timing circuit for controlling the operation of the time voltage converting circuit 5, the analogue switch 6, and the memory circuit 7.

Another monostable multi-vibrator circuit 10 is triggered by the rising of the every second pulse of the monostable multivibrator 2 for forming a rectangular wave having a shorter width $t_2$ (for example 2 ms) than the pulse width $t_1$, which signal controls the operation time of the afore-mentioned judging in the window comparator 9 and re-sets (clears) the time voltage converting circuit 5 and the memory circuit 7 at the falling of the pulse wave of width $t_2$, wherein $t_2$ means the comparison time of the pulse intervals and the deduction $(t_1-t_2)$ means the re-set time of the above cited circuits.

The output from the second monostable multi-vibrator circuit 10 is, together with the output from the window comparator 9, applied to an AND circuit 11, for making the counter 12, of arrhythmias number operative only when both signals come on simultaneously The wave form diagram on FIG. 3 shows the timewise relationship (phase) between operations of each circuit on FIG. 2. Numerals alloted to each wave form are all identical to those in FIG. 1, only different in being added "a" letter to each number, i.e., 1a means an output signal from the pulsation detector 1, 2a means an output pulse wave form from the monostable multivibrator circuit 2, 5a indicates an output wave form, a memory circuit wave form, and a re-set timing from the time voltage converting circuit 5, 9a is an output wave form of the window comparator 9, 10a is an output wave form of the pulse width $t_2$ delivered from the monostable multi-vibrator circuit 10, and 11a shows a detected output wave form of arrhythmias.

Limitation to the pulse width $t_1$ of the first monostable multi-vibrator circuit 2 must be commented next.

Assume the upper limit of the pulse number observed on a human body be 150 beats per minute, a pulse interval $T_1'$ is:

$$T_1' = 60{,}000 \ ms/150 = 400 \ ms$$

And assume again the next pulse interval $T_2'$ be 25% increase (the upper limit assumed in this embodiment), then:

$$T_2' = 1.25 \ T_1 = 500 \ ms$$

Allow 0.05% or less error to the comparison of the two approximate pulse intervals $(T_1'-t_1)$ and $T_2'-t_1)$, then:

$$(T_2'-t_1)/(T_1'-t_1) = (500-t_1)/(400-t_1) \doteq 1.25+0.005 \quad (1)$$

is established.

The value of $t_1$ can be got by solving the opp. equation $$t_1 \leq 7.85 \ ms$$

This $t_1$ is wished in principle to be zero, as it is a cause of the error; it can not be in fact too extremely small, because this $t_1$ is necessitated as a least span of time, for the sum of comparison time in the window comparator 9 and the re-set time in the memory circuit 7, etc. In this embodiment $t_1$ is necessitated to be 7 ms or less, on the assumption of the error be 0.05% or less (if $t_1$ is equal to zero, the left side of the opp. equation (1) would be 1.25).

It is further desired that the arrhythmias judged by the instrument in this embodiment may be visually observed or easily sensed by any other indication means. As means of indication one of the following types is desirable for this invention, which conditions inexpensiveness and simpleness as its essence.

(1) Two-colored lamp indication (for example green and red) employing lamp A and B:

The lamp A lights for only pulse interval $(T_1-t_1)$ green, receiving signals from the gate circuit 4. The lamp B lights, next, the following pulse interval $(T_2-t_1)$ green again. When an output of the arrhythmia is delivered from the window comparator 9 due to the comparison of the both pulse intervals, only the next interval duration $(T_1-t_1)$ the lamp A will be lit red. The existence of arrhythmia, if any, can be clearly seen by the operator of the instrument. The occurring frequency of the arrhythmias is also detected by counting the number of the illuminations of the red lamp A, using, for example, either a visual or mechanical counting method.

(2) Two-colored lamp indication (for example green and red) employing only one lamp A:

The lamp A lights green, receiving signals from the gate circuit 4, during the duration of time $(T_1-t_1)$, and during the succeeding duration of time $(T_2-t_1)$ it lights green again. If there appears an output of arrhythmia from the comparison of both pulse intervals, the lamp A lights red during the next duration of time $(T_1-t_1)$, thereby enabling the existence of arrhythmia to be observed visually. The intermission time between the green light of the A lamp for the first $(T_1-t_1)$ duration and that for the second duration of $(T_2-t_1)$ is too short for human eyes (bare eyes) to perceive the gap or interval of the lighting. It seems as if the two times of lighting were with out a break. It is required to put inbetween some proper length of non-light time.

(3) It is possible, as still another method, to dispose a plurality of lamps for counting the number of arrhythmias, each lamp being lit for each occurring of arrhythmia, one after another. By counting the number of lamps lit during a predetermined period of time the frequency of the arrhythmias can be observed. The number of arrhythmias may be of course digitally indicated instead of lighting of the lamps.

Other embodiments will be described with reference to FIGS. 4 and 5. Explaining based on FIG. 4, by referring to FIG. 5, pulse detector 21 is to detect pulse signals for delivering them to the monostable multi-vibrator circuit 22 (a first monostable multi-vibrator), wherein they are shaped into pulses of rectangular wave (pulse width $t_1$). The signal from the flip-flop circuit 23, which has been triggered by the falling of the rectangular wave, functions to make the clock pulses from a clock pulse generator 25 pass, via the gate circuit 24, through an AND circuit 26, and consequently makes a counter 27 count the number of clock pulses a short inter-distance. The number of clock pulses are to be memorized by an A memory circuit 28. It means that the number of clock pulses counted during the time $(T_1-t_1)$, rest of the time of a certain pulse interval $T_1$ minus the pulse width $t_1$ of the rectangular wave, is memorized in the A memory circuit 28 as an object of comparison.

As to the pulse interval $T_2$, which succeeds immediately after the previous pulse interval $T_1$, the number of clock pulses from the rising to the falling of the rectangular wave $(T_2-t_1)$ is to be memorized just similarly to the aforementioned way in a B memory circuit 29.

The memorized number of pulses in the B memory circuit 29 shall be divided by the memorized number of pulses in the A memory circuit 28 in a division circuit 31, that is, B memory number of pulses ÷ A memory number of pulses.

A second monostable multi-vibrator circuit 30 is such a circuit that is triggered by every other rising of the rectangular wave of the first monostable multi-vibrator circuit 22 and forms a rectangular wave having a pulse width $t_2$, which is shorter in width than $t_1$, within which time $t_2$ the division and the later stated comparison can be completed.

A digital window comparator 32 compares the signals of computed value from the division circuit 31 with the predetermined allowance value (i.e. the upper and lower limits) for delivering signals, only when the comparison result is or out of the allowable range, to an arrhythmia counter 33.

Figure 5:
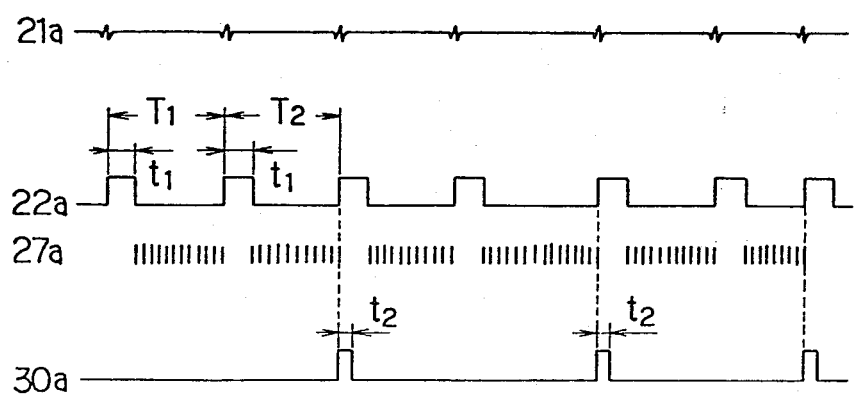
FIG. 5 is a diagram of wave forms showing phase relationship of each circuit in the arrhythmia detecting mechanism of FIG. 4.

The wave form diagram in FIG. 5 shows the phase relationship among the circuits shown in FIG. 4. Numerals used in FIG. 5 are all identical to those in FIG. 4, only being added "a" letter to each numeral, in other words, 21a is the output of the pulsation detector 21, 22a is the output pulse wave form of the monostable multi-vibrator circuit 22, 27a is the wave form of the clock pulses input to the counter 27, and 30a is the output wave form of the monostable multi-vibrator circuit 30.

This embodiment is featured in dispensing, unlike the previous one, with conversion of time into voltage, when the comparison of pulse intervals is carried out, but capable of direct comparison of the counted values of the clock pulses, in a way very simple. It has made this embodiment smaller (more compact) in size and more convenient in carrying.

Summarizing characteristic effects, common in all embodiments, of the invention mechanism, the following items can be enumerated.

(1) By means of a unique change of conception from the conventional direct comparison of the whole duration of pulse interval $T_1$ and $T_2$ to the effective limited comparison only of the approximate time duration $(T_1-t_1)$ and $(T_2-t_1)$, suitable selection of $t_1$ time, width of the pulse, made it possible to repeatedly employ the memory circuits of minimum number necessitated, within the sphere of error substantially of no harm to the precision. With the adoption of this concept, mechanism of the arrhythmia detector has been made quite simple in construction and the resultant error small enough to be neglected.

(2) By introducing a suitable pulse width $t_1$ into the initial stage of the pulse interval, and by dividing this $t_1$ time into two parts for finishing the pulse interval comparison within the first half $t_2$ of the $t_1$ and completing the re-set of the memory circuit, etc. during the rest of the time $(t_1-t_2)$. It has consequently succeeded in making all of the preparation for the succeeding operations finish within the $t_1$ time.

(3) The above-mentioned concept has made the invention arrhythmia detector and, method far simpler in structure, far lighter in weight, far more convenient for carrying, far easier in clinical use, far less expensive in cost, and far more favorable for being attached to the sphygmomanometer.

What is claimed is:

1. A method of arrhythmia detection using a sphygomanometer with an arrhythmia detecting mechanism, wherein diagnosis of arrhythmia is done simultaneously with the blood pressure measurement, comprising the steps of detecting arrythmia by comparing the ratio of two consecutive physiological pulse interval times with a predetermined allowable range value, determining an arrythmia if said ratio value is out of said allowable range, setting said two consecutive pulse interval times as one duration time $T_1$ from a base point of a said pulse appearing or disappearing to the next similar base point of a said pulse appearing or disappearing, taking a succeeding duration of time $T_2$ in the identical way between each two similar base points, said arrhythmia detecting method being characterized by the steps of simultaneous derivation of arrythmia system input from the Korotkoff or physiological pulse pressure waveforms of the sphygmomanometric portion of the system, electrically forming a first pulse from said physiological pulse detecting; calculating two time values $(T_1-t_1)$ and $(T_2-t_1)$ by deducting from one pulse interval $T_1$ and the next pulse interval $T_2$ respectively the pulse interval $t_1$ of said first pulse, said time values being made the objects of the pulse interval comparison; completing said comparison within the pulse duration time of a second pulse triggered at every second rising of said first pulse width $t_1$, and clearing the memory of pulse interval comparison within the time duration $(t_1-t_2)$, i.e., from the rising of said second pulse to the falling of said first pulse.

2. A method as claimed in claim 1, and the steps of indicating blood pressure values by using logic circuitry for recognizing the Korotkoff sounds and an indicating means for indicating blood pressure values in response to the output from said logic circuitry.

3. A method as claimed in claim 2, and the step of digitally indicating blood pressure values by using light emitting diodes (LEDs).

4. A method as claimed in claim 1, wherein said arrhythmia detecting steps further comprise:
    converting a pulse interval, which spans the time from the appearance point or the disappearance point of a pulse to the appearance point or the disappearance point of the next pulse, that is, from one base point to the next base point in the same phase, into another physical amount corresponding to said pulse interval;

comparing said converted physical amount with a predetermined criterion using a window comparator in order to check whether said physical amount is within said limit of allowance; and indicating arrhythmia by using the output of said window comparator to deive an indicating means.

5. A method as claimed in claim 4, wherein said arrhythmia detecting steps further comprise:

forming a pulse with a rectangular wave with the pulse width $t_1$ in response to signals from a pulse to be detected using a first pulse forming circuit;

memorizing the converted physical amount from said converting circuit using a memory circuit;

a timing circuit causing a least said converting circuit and said memory circuit to function in an orderly manner and without error by using a timing circuit;

calculating the physical amount, which corresponds to the deducted value, respectively from said one pulse interval $T_1$ and the next pulse interval $T_2$ minus said pulse width $t_1$, as the objects of pulse interval comparison by using an operation circuit;

forming said pulse with a pulse width $t_2$, which is shorter than the pulse width $t_1$, capable of finishing said comparison of pulse interval within the duration of time $t_2$, a second pulse forming circuit and clearing said memory circuit within the duration of time rest $(t_1-t_2)$; and using the output of said first pulse forming circuit as the input to a flip-flop circuit which in turn outputs to said second pulse forming circuit and said timing circuit.

6. A method as claimed in claim 5, wherein said converting circuit converts the time $(T_1-t_1)$ from the first pulse to the second pulse in the pulse signal which is output in the first pulse forming circuit and synchronized with the pulse seconds to be detected into a voltage; said operation circuit receives the converted voltage value through said memory circuit and computes and produces a voltage increased in amount and another voltage decreased in amount respectively by a certain predetermined percentage for inputting both voltage values to said window comparator as the upper and lower limits, and said indicating means indicating the existence of arrhythmia when the voltage value of the time $(T_2-t_1)$ ranging from the second pulse to the third pulse, which is input directly from said converting circuit to said window comparator, is out of the range between said upper limit and lower limit.

7. A method as claimed in claim 6, wherein said second pulse forming circuit produces a rectangular wave with a pulse width $t_2$ at every second pulse out of the pulses output from said first pulse forming circuit, and wherein an AND circuit is disposed for receiving said rectangular wave signals and those from said window comparator and delivers signals to said arrhythmia indicating means only when said both signals are input to said AND circuit at the same time.

8. A method as claimed in claim 5, wherein said converting circuit converts the time $(T_1-t_1)$ from the first pulse to the second pulse, and the time $(T_2-t_1)$, from the second pulse to the third pulse, of the pulse signal which is output in the first pulse forming circuit and synchronized with the pulse sounds to be detected, into the number of clock pulses, said memory circuit is composed of a pair of circuits for respectively memorizing such two numbers of clock pulses, said operation circuit is a division circuit for determining the ratio of said two clock pulses input through said memory circuit, and said window comparator compares the ratio of said two kinds of clock pulse numbers with the predetermined allowance value, for signalling, when said ratio gets out of the allowable range, said indicating means.

9. A method as claimed in claim 8, wherein said second pulse forming circuit produces a rectangular wave with the pulse width $t_2$ at every second pulse our of the pulses output from said first pulse forming circuit, and said rectangular wave signal thus produced is input to said division circuit.

10. A method as claimed in any one of claims 5 to 9, wherein the pulse width $t_2$ of the pulse signal output from said first pulse forming circuit is 7 milliseconds or less.

11. A method as claimed in any one of claims 4 to 9, wherein said indicating means digitally indicates the number of arrythmias using light emitting diodes (LEDs).

* * * * *